US005429142A

United States Patent [19]

Szabo et al.

[11] Patent Number: 5,429,142

[45] Date of Patent: Jul. 4, 1995

[54] SURGICAL VIDEO SYSTEMS COVER

[75] Inventors: Steve G. Szabo, Largo; John A. Monty, St. Petersburg, both of Fla.

[73] Assignee: Linvatec Corporation, Largo, Fla.

[21] Appl. No.: 68,430

[22] Filed: May 27, 1993

[51] Int. Cl.[6] ........ A61B 19/00; A61B 19/08

[52] U.S. Cl. ........ 128/849; 128/853

[58] Field of Search ........ 128/849, 845, 846, 850–856; 74/608, 609, 612, 613; 355/230, 231

[56] References Cited

U.S. PATENT DOCUMENTS

| | | | |
|---|---|---|---|
| 3,060,932 | 10/1962 | Pereny | 128/849 |
| 3,667,458 | 6/1972 | Krebs | 128/853 |
| 3,742,944 | 7/1973 | Sease . | |
| 3,820,536 | 6/1974 | Anspach | 128/853 |
| 4,041,942 | 8/1977 | Dougan et al. . | |
| 4,185,625 | 1/1980 | Morris . | |
| 4,266,663 | 5/1981 | Geraci . | |
| 4,275,719 | 6/1981 | Mayer | 128/849 |
| 4,408,692 | 10/1983 | Sigel et al. . | |
| 4,484,845 | 11/1984 | Pennella | 74/608 |
| 4,627,427 | 12/1986 | Arco | 128/853 |
| 4,736,762 | 4/1988 | Wayman | 128/846 |
| 4,886,049 | 12/1989 | Darras . | |
| 4,976,274 | 12/1990 | Hanssen . | |
| 4,999,895 | 3/1991 | Hirose | 74/608 |
| 5,020,546 | 6/1991 | Russo | 128/849 |
| 5,080,108 | 1/1992 | Roth . | |
| 5,325,970 | 7/1994 | Dillon | 150/165 |

*Primary Examiner*—Michael A. Brown
*Attorney, Agent, or Firm*—Rosenblatt & Associates

[57] ABSTRACT

The present invention allows operating room personnel to easily and expeditiously drape electronic surgical devices, such as video monitors, cameras, lights, and power sources. This invention relates to a disposable, four-sided surgical drape that maintains a protective cover over the equipment. The drape consists of an opaque material on the two side panels and the top panel of the drape. The front panel is preferably formed of a clear, pliable plastic material, with a rectangularly shaped front panel cutout at the top portion of the panel. This front panel cutout and the attached adhesive strip allow surgical personnel to visually access the video monitor and seal the front panel to the monitor. The rear and underside of the cover are open to ensure proper ventilation and easy application.

22 Claims, 1 Drawing Sheet

10
A
6
20
14
2
18
26
24
22
8
12
16

SURGICAL VIDEO SYSTEMS COVER

FIELD OF THE INVENTION

This invention relates generally to the field of medical instruments, and more particularly to a disposable, four-sided surgical drape that is used to cover electronic surgical devices, such as video monitors, cameras, lights, and power sources.

BACKGROUND OF THE INVENTION

Typically, equipment is not covered in the operating room, yet it has the potential to be contaminated. Some operating room staff may choose to protect their equipment by using any available material.

When electronic devices are outside the surgical field, then the surfaces of these devices are exposed to water and body fluids that are splashed about during the surgical procedure. This exposure results in potential contamination, difficult clean-up, and it jeopardizes the electronic components of the devices.

The present invention overcomes the problems of the prior art by providing a specially designed four-sided disposable cover which enables easy application and a cost-efficient method of protecting electronic devices from direct and repeated exposure to fluids which may be sprayed during surgery.

SUMMARY OF THE INVENTION

The present invention relates to a four-sided disposable surgical drape which is used to cover stackable electronic video systems such as a monitor, camera, light source, recorder, or printer. The drape consists of an opaque disposable material on the two side panels and the top panel to ensure low-cost, efficient protection. The edges along the rear of the side panels are capable of being taped onto the back side of the equipment to secure the drape in place. The drape is not sterile, but can be sterilized. Since the covered equipment is not in the sterile field, the drape is not required to be sterile.

The front panel is constructed of a clear plastic, pliable material which allows visibility and access to the electronic controls. The top of the front panel is designed with a substantially rectangular cutout to accommodate the monitor screen, thus ensuring that the visual images on the screen are uncompromised. The periphery of the cutout is provided with an adhesive which sticks to the monitor and seals the drape onto the monitor screen.

The rear of the drape is open to allow proper ventilation of the electronic equipment. The underside of the drape is also open to allow easy application of the drape over the stackable equipment or by slidably pulling the drape onto the electronic equipment, front to rear. Operating room personnel need only to secure the adhesive strip onto the monitor screen and tape the rear of the drape onto the side of the electronic equipment. The rear is left exposed for ventilation. The screen of the monitor is the only exposed component of the electronic equipment. This results in minimal clean-up after completion of the surgery.

DESCRIPTION OF THE PREFERRED EMBODIMENT

Figure 1:
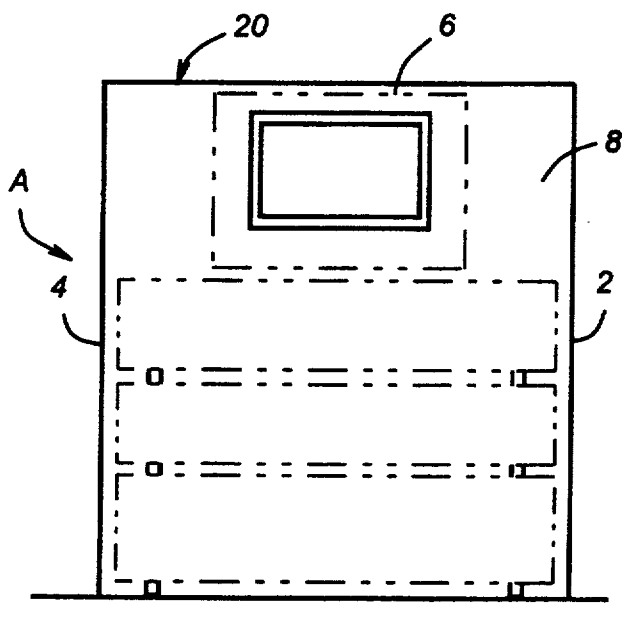
FIG. 1 is a front view of the invention in place over a monitor and other equipment.
Figure 2:
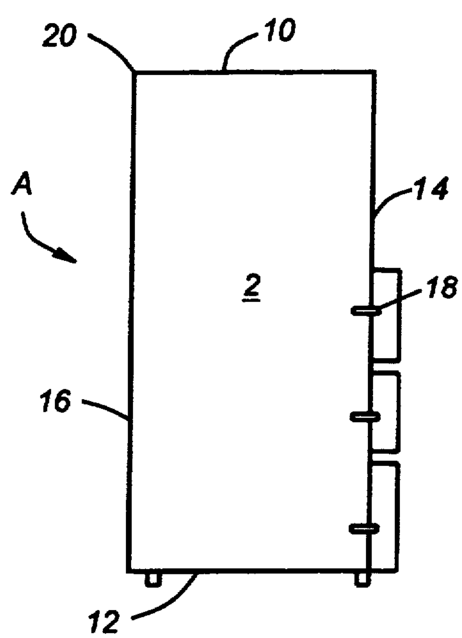
FIG. 2 is a side view of the invention.

The apparatus A is illustrated in FIG. 1. The apparatus A is made of four substantially rectangular panels, two side panels 2 and 4, one top panel 6, and one front panel 8. The two side panels 2 and 4 are preferably made of a polymeric material which is a flexible opaque, low-cost draping material (for example, nonwoven polyethylene). The parameters of side panel 2, as illustrated in FIG. 2, are defined by a transversely extending top edge 10, a transversely extending bottom edge 12, and a pair of longitudinally extending opposed side edges 14 and 16. The longitudinally opposed side edges 14 and 16 are slightly longer than the electronic equipment that is covered to facilitate securing edge 12 to the floor or table top for sealing contact. The top extending edge 10 and bottom extending edge 12 are preferably slightly shorter in length than the equipment that is encased between the two side panels 2 and 4. Side edge 14 is capable of being taped 18 to the side of the electronic equipment to secure the side panel in place. Panels 2 and 4 can be longitudinally taped, integrally formed with, or otherwise secured to panel 8 along edges 16 or they can be loosely fitted for subsequent longitudinal seam sealing by operating room personnel after fitting the drape apparatus A to the equipment. The method of securing edge 14 to the equipment can be varied without departing from the spirit of the invention. The electronic equipment is capable of extending beyond the perimeter of edge 14 because the rear of the drape is open to ensure proper ventilation of the equipment. Side panels 2 and 4 are preferably identical. Thus, FIG. 2 is similarly illustrative of side panel 4.

Referencing FIGS. 1 and 2, side panels 2 and 4 fold into top panel 6 to form a substantially U-shaped configuration. Top panel 6 is preferably made of the same polymeric material. A transversely extending forward edge 20 on the proximal edge of the top panel 6 and the longitudinally extending side edges 16 on side panels 2 and 4 define the border of attachment of the front panel 8. Panels 2,4,6,8 can be made of several components or less. For example, panels 2,4, and 6 can be one piece. Alternatively, a single piece of material properly stitched or assembled can serve as panels 2,4,6,8.

Figure 3:
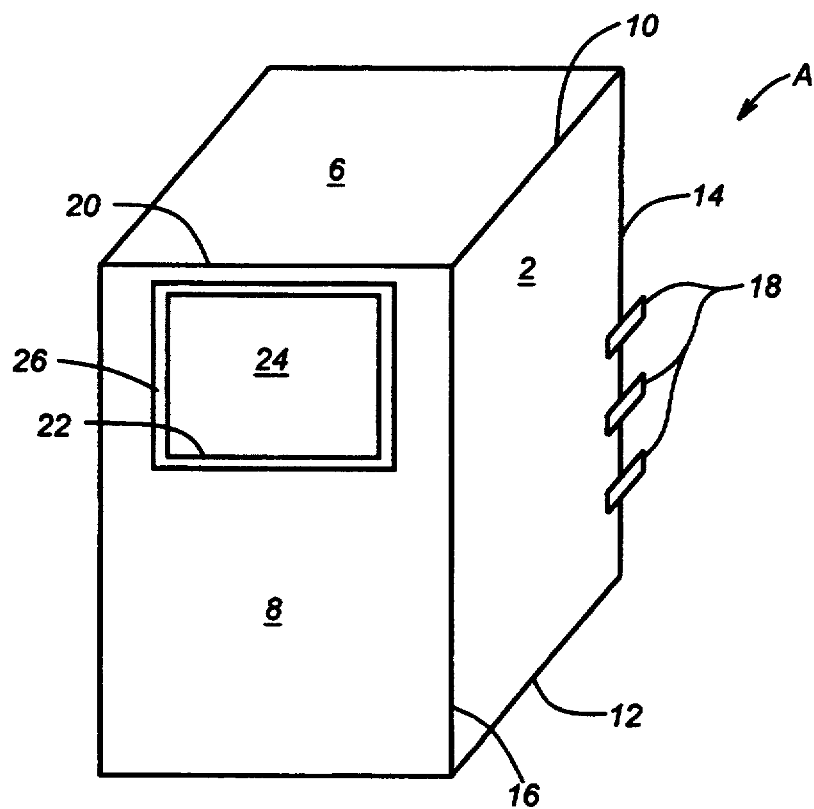
FIG. 3 is an isometric view of the invention not showing any covered equipment.

FIG. 3 is illustrative of front panel 8. Front panel 8 is constructed of a translucent, pliable, water-resistant material, preferably polymeric, to enable the surgeons and the operating room personnel to monitor and easily access the electronic controls through panel 8. The front panel 8 has a preformed substantially rectangular opening 22, congruently sized to accommodate the monitor screen 24. An adhesive strip 26 borders the monitor screen opening 22 on all four sides to ensure that the drape is sealed onto the monitor screen 24 to protect against the flow of contaminants and water onto the electronic equipment.

Numerous variations within the scope of the appended claims will be apparent to those skilled in the art in light of the foregoing description and accompanying drawings. The foregoing disclosure and description of the invention are illustrative and explanatory thereof, and various changes in the size, shape and materials, as well as in the details of the illustrated construction, may be made without departing from the spirit of the invention.

We claim:

1. A drape for surgical equipment having exposed and nonexposed faces, and further comprising at least a monitor and controls, comprising:

at least one panel to substantially cover exposed faces of the equipment while supported by the equipment;

said panel having at least one first opening, said first opening in substantial alignment with the monitor to allow unimpeded viewing of the monitor through said opening during use; and said panel further comprising at least one second opening, said second opening disposed adjacent at least one nonexposed face of the equipment to facilitate operation of the equipment and to facilitate applying said panel over equipment by moving said second opening over the equipment so that the exposed faces of the equipment are covered for a surgical procedure.

2. A drape for surgical equipment having exposed and nonexposed faces and further comprising at least a monitor and controls, comprising:

at least one panel to substantially cover exposed faces of the equipment;

said panel having at least one first opening, said first opening in substantial alignment with the monitor to allow substantially unimpeded viewing of the monitor through said opening during use;

said panel further comprising at least one second opening, said second opening disposed adjacent at least one nonexposed face of the equipment to facilitate operation of the equipment and to facilitate applying said panel over equipment by moving said second opening over the equipment so that the exposed faces of the equipment are covered for a surgical procedure; and said panel further comprising a transparent flexible segment disposed adjacent the controls of the equipment to allow sight and operation of such controls while simultaneously keeping them covered.

3. The drape of claim 2, further comprising:

securing means adjacent the periphery of said first opening for securing said panel around a monitor.

4. The drape of claim 3, wherein:

said second opening having the substantial shape of a nonexposed face, thereby allowing said panel to be mounted from the front of the equipment and pulled back to cover the exposed faces of the equipment with said first opening substantially aligned with the monitor.

5. The drape of claim 4, wherein:

said panel is multifaceted comprising:

a top;

a plurality of sides;

said front and sides connected to said top on at least one edge.

6. The drape of claim 5, wherein:

said first opening and said transparent flexible segment are disposed in said front.

7. The drape of claim 6, wherein:

said top and sides forming an edge which is disposed adjacent the nonexposed face of the equipment to facilitate securing said top and sides adjacent the nonexposed face of the equipment.

8. The drape of claim 7, further comprising:

a selectively sealable edge connection between each of said sides and said front.

9. The drape of claim 7, further comprising:

a selectively engageable scaled edge connection between each of said sides and said front.

10. A drape for articles, comprising:

at least one panel to substantially cover the article while being supported by the article;

said panel having at least one first opening capable of allowing unimpeded visibility of the article during use;

said panel further defining at least one second opening, said second opening parallel to said first opening to faciltate mounting the panel to the article by sliding it over the article.

11. A drape for articles, comprising:

at least one panel to substantially cover the article while being supported by the article;

said panel having at least one first opening comprising a transparent flexible segment disposed adjacent the article to allow sight and enable operation of the article while simultaneously covering the article;

said panel further defining at least one second opening, said second opening parallel to said first opening to facilitate mounting the panel to the article by sliding it over the article.

12. The drape of claim 11, further comprising:

securing means adjacent the periphery of said first opening for securing said panel to the article.

13. The drape of claim 12, wherein:

said second opening defining an open back on said panel, thereby allowing said panel to be mounted from the front of the article and pulled back to cover the article.

14. The drape of claim 13, wherein:

said panel is multifaceted comprising:

a top;

a plurality of sides;

said front and sides connected to said top on at least one edge.

15. The drape of claim 14, wherein:

said first opening and said transparent flexible segment are disposed in said front.

16. The drape of claim 15, wherein:

said top and said sides forming at least one edge to facilitate securing top and sides to the article.

17. The drape of claim 16, further comprising:

a selectively sealable edge connection between each of said sides and said front.

18. The drape of claim 16, further comprising:

a selectively engageable sealed edge connection between each of said sides and said front.

19. A drape for covering operating room equipment, comprising:

a plurality of panels, comprising:

a top;

three sides forming an open back;

whereupon operating room equipment can be covered by slipping said open back over the equipment.

20. The drape of claim 19, wherein:

said panels are formed of a polymeric nonwoven material.

21. The drape of claim 19, further comprising:

at least one opening in one of said side panels to allow viewing of the equipment therethrough;

securing means around the periphery of said opening to secure said side panel containing said opening to the equipment.

22. A drape for covering operating room equipment, comprising:

a plurality of panels, comprising:

a top;

three sides forming an open back, said sides being releasably connected to each other to facilitate installation of said drape;

whereupon operating room equipment can be covered by slipping said open back over the equipment.

* * * * *